(12) United States Patent
Tucker et al.

(10) Patent No.: US 10,424,804 B2
(45) Date of Patent: Sep. 24, 2019

(54) OPTIMIZATION OF THE CERIUM-HYDROGEN REDOX FLOW CELL

(71) Applicants: Michael C. Tucker, Piedmont, CA (US); Adam Z. Weber, Lafayette, CA (US)

(72) Inventors: Michael C. Tucker, Piedmont, CA (US); Adam Z. Weber, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 210 days.

(21) Appl. No.: 15/582,225

(22) Filed: Apr. 28, 2017

(65) Prior Publication Data
US 2017/0338508 A1 Nov. 23, 2017

Related U.S. Application Data

(60) Provisional application No. 62/329,782, filed on Apr. 29, 2016.

(51) Int. Cl.
| | | |
|---|---|---|
| H01M 6/18 | (2006.01) |
| H01M 8/18 | (2006.01) |
| C07F 5/00 | (2006.01) |
| H01M 8/1004 | (2016.01) |
| H01M 4/90 | (2006.01) |

(Continued)

(52) U.S. Cl.
CPC .............. *H01M 8/188* (2013.01); *C07F 5/00* (2013.01); *H01M 4/9041* (2013.01); *H01M 4/92* (2013.01); *H01M 8/1004* (2013.01); *C01B 3/0047* (2013.01); *Y02E 60/528* (2013.01)

(58) Field of Classification Search
CPC .. H01M 8/188; H01M 8/1004; H01M 4/9041; H01M 4/92
See application file for complete search history.

(56) References Cited

U.S. PATENT DOCUMENTS

| | | | |
|---|---|---|---|
| 2005/0244707 A1* | 11/2005 | Skyllas-Kazacos | ........................ B60L 11/1894 429/105 |
| 2006/0251945 A1* | 11/2006 | Song | ................... H01M 8/0239 429/483 |

FOREIGN PATENT DOCUMENTS

WO    WO 2015/100216 A1    7/2015

OTHER PUBLICATIONS

Yufit et. al., "Development of a Regenerative Hydrogen-Vanadium Fuel Cell for Energy Storage Applications", Journal of the Electrochemical Society, vol., No. 160 (6), pp. A856-A861 (2013).

(Continued)

*Primary Examiner* — Jane J Rhee

(57) ABSTRACT

The Ce—$H_2$ redox flow cell is optimized using commercially-available cell materials. Cell performance is found to be sensitive to the upper charge cutoff voltage, membrane boiling pretreatment, methanesulfonic-acid concentration, (+) electrode surface area and flow pattern, and operating temperature. Performance is relatively insensitive to membrane thickness, Cerium concentration, and all features of the (−) electrode including hydrogen flow. Cell performance appears to be limited by mass transport and kinetics in the cerium (+) electrode. Maximum discharge power of 895 mW $cm^{-2}$ was observed at 60° C.; an energy efficiency of 90% was achieved at 50° C. The Ce—$H_2$ cell is promising for energy storage assuming one can optimize Ce reaction kinetics and electrolyte.

23 Claims, 13 Drawing Sheets

(51) Int. Cl.
*H01M 4/92* (2006.01)
*C01B 3/00* (2006.01)

(56) References Cited

OTHER PUBLICATIONS

Yufit et. al., "Development of a Regenerative Hydrogen-Vanadium Fuel Cell for Energy Storage Applications", Journal of the Electrochemical Society, vol. 160, No. (6), pp. A856-A861 (2013).
Cho et. al., "Cyclic Performance Analysis of Hydrogen/Bromine Flow Batteries for Grid-Scale Energy Storage", ChemPlusChem, vol. 80, pp. 402-411 (2015).
Cho et. al., "Optimization and Analysis of High-Power Hydrogen/Bromine-Flow Batteries for Grid-Scale Energy Storage", Energy Technology, vol. 1, pp. 596-608 (2013).
Cho et. al., High Performance Hydrogen/Bromine Redox Flow Battery for Grid-Scale Energy Storage:, Journal of the Electrochemical Society, vol. 159, No. 11., pp. A1806-A1815 (2012).
Dewage et. al., "A novel regenerative hydrogen cerium fuel cell for energy storage applications", Journal of Materials Chemistry A, vol. 3, pp. 9446-9450 (2015).
Tucker et. al., "Optimization of electrode characteristics for the Br2/H2 redox flow cell", Journal of Applied Electrochemistry, vol. 45, pp. 11-19, (2015).
Lin et. al., "Vacuum-Tight Thin-Layer Spectroelectrochemical Cell with a Doublet Platinum Gauze Working Electrode", American Chemical Society, vol. 57, pp. 1498-1501, (1985).
International Application Published as WO 2015/09555 AI on Jun. 25, 2015, for International Application No. PCT/US2014/071214.
Tucker et al., "Cerium-Hydrogen Redox Flow Cell Optimization." The Electrochemical Society, Abstract, 2016.
Yufit et al., "Development of a Regenerative Hydrogen-Vanadium Fuel Cell for Energy Storage Applications." Journal of the Electrochemical Society, vol. 160, No. 6, pp. A856-A861, Mar. 30, 2013.
Xie et al., "Processing and Pretreatment Effects on Vanadium Transport in Nafion Membranes" Journal of the Electrochemical Society, vol. 163, No. 1, pp. A5084-A5089, Oct. 13, 2015.
Dewage et al., "Study of Loss Mechanisms Using Half-Cell Measurements in a Regenerative Hydrogen Vanadium Fuel Cell." Journal of the Electrochemical Society, vol. 163, No. 1, pp. A5236-A5243, Dec. 1, 2015.
Xie et al., "The developments and challenges of cerium half-cell in zinc-cerium redox flow battery for energy storage." Electrochimica Acta, vol. 90, pp. 695-704, Dec. 25, 2012.
Walsh et al., "The Development of Zn—Ce Hybrid Redox Flow Batteries for Energy Storage and Their Continuing Challenges." Chem Plus Chem, vol. 80, No. 2, pp. 288-311, Nov. 13, 2014.
Tucker et al., "Improvement and analysis of the hydrogen-cerium redox flow cell." Journal of Power Sources, vol. 327, pp. 591-598, Jul. 26, 2016.
H.M.H. Dewage, "Investigation of Hydrogen based Redox Flow Batteries", Imperial College London Department of Earth Science and Engineering, Thesis, Jun. 2016.
C. Wanh, "Development of Low Cost PEMFC Metal Bipolar Plate", Fuel Cell Seminar, Oct. 31-Nov. 3, 2011.
M. Tucker, et al., "Understanding and Optimizing the H2/Br2 Redox Flow Battery for Grid-Scale Energy Storage", 2nd MRES Northeastern, Aug. 19, 2014.
M. Tucker, et al., "Impact of membrane characteristics on the performance and cycling of the Br2—H2 redox flow cell", Journal of Power Sources 284 (2015) 212-221.

* cited by examiner

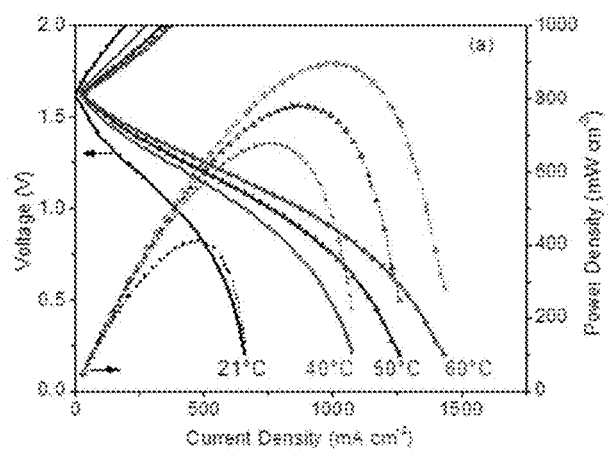 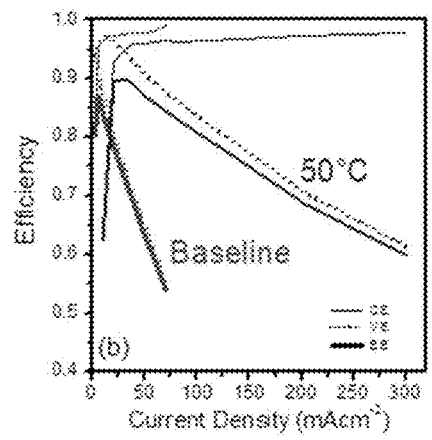
FIG. 10A
FIG. 10B

OPTIMIZATION OF THE CERIUM-HYDROGEN REDOX FLOW CELL

CROSS REFERENCE TO RELATED APPLICATIONS

This application claims priority to U.S. Provisional Application Ser. No. 62/329,782 filed Apr. 29, 2016, which application is incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

Field of the Invention

The present invention relates to the field of Redox flow batteries (RFB).

Related Art

Redox flow batteries (RFB) with various solution chemistries are being developed for large-scale energy storage. Advances in redox-active species, electrocatalysts, and separators are required to meet the stringent cost and durability requirements for affordable storage, and recent years have seen many new contributions to the field, which also highlight the necessary areas for improvement.

One promising class of RFB utilizes hydrogen gas as the negative working fluid, and an aqueous solution of redox-active species as the positive working fluid. Hydrogen is inexpensive, can be electrochemically compressed to minimize storage volume, and has excellent reaction kinetics. Liquid that crosses through the membrane from the (+) to (−) side is easily separated from the hydrogen gas for return to the positive-electrode tank, simplifying electrolyte balancing. With only one side of the cell containing liquid, pumping and shunt-current losses are expected to be minimized. Furthermore, the adoption of cell architecture derived from mature high-power proton-exchange-membrane (PEM) fuel cells provides excellent cell performance metrics.

Various RFBs with hydrogen (−) electrode have been reported. Halogen-hydrogen cells using primarily $Cl_2$ and $Br_2$ have been reviewed recently, and provide among the highest reported power and efficiency metrics for RFBs due to fast, reversible kinetics and moderate self-discharge.

For example, 1.4 W $cm^2$ discharge power density, 90% peak energy efficiency, and 80% energy efficiency at 0.4 A $cm^2$ were achieved at room temperature for the $Br_2$—$H_2$ system, which has an open circuit voltage (OCV) of 1.09 V.

The Fe—$H_2$ cell provides the potential for extremely inexpensive and benign iron-based electrolyte, however at a rather low cell potential (0.77V). Optimization of this cell, including addition of supporting electrolyte, achieved peak power density of 250 mW $cm^2$ and energy storage efficiency of 78%. Cost analysis suggested that although the active materials are very inexpensive, cell performance was too low to be economically attractive given the cost of cell/stack materials.

The V-$H_2$ system offers open-circuit potential of 1 to 1.2 V, depending on vanadium concentration. Proof-of-concept work demonstrated moderate performance (114 mW $cm^{-2}$) and 60% energy efficiency. The main limitations for this cell are thought to be vanadium diffusion in the (+) electrode and interaction of crossover vanadium with the Pt (−) catalyst.

SUMMARY

One innovative aspect of the subject matter described in this disclosure can be implemented in a redox flow cell comprising a separator, a negative electrode in contact with a reactive fluid, a liquid electrolyte comprising reactants, and a positive electrode comprising at least one metal mesh layer in contact with the liquid electrolyte. The negative electrode is isolated from the positive electrode by the separator.

In some implementations, the separator comprises an ion exchange membrane (IEM) or a nanoporous separator.

In some implementations, the positive electrode comprises a 3-dimensional porous flow-through structure.

In some implementations, the reactive fluid is a hydrogen gas. In some implementations, the reactants comprise Cerium (IV) methanesulfonate (MSA).

In some implementations, the positive electrode comprises a stack of metal meshes. In some implementations, the positive electrode comprises between 1-12 stacks of woven platinum meshes. In some implementations, the positive electrode comprises a nanostructured thin-film (NSTF) platinum catalyst layer.

In some implementations, the redox flow cell comprises a diffusion barrier layer comprising at least one of Daramic, Celgard, Millipore, Amer-sil, or Durapore.

In some implementations, a catalyst layer is in contact with the separator on the negative electrode side of the separator. In some implementations, a catalyst layer is in contact with a microporous layer on the negative electrode side of the separator.

In some implementations, a gas diffusion layer is disposed on the negative electrode side of the separator.

In some implementations, the separator comprises a proton exchange membrane (PEM). In some implementations, the separator comprises an anion exchange membrane (AEM). In some implementations, the separator comprises a thin (0.025-0.05 mm), preboiled membrane.

In some implementations, a diffusion barrier layer is configured to maximize cell round-trip energy efficiency.

In some implementations, an electrolyte composition comprises approximately 0.6 M Cerium and 5 M MSA.

In some implementations, the negative electrode comprises a 0.4 mg $cm^{-1}$ Pt-on-carbon catalyst layer.

In some implementations, the cell is operated at a temperature range between 21° C.-60° C. In some implementations, the cell is operated at a temperature range between 50° C.-60° C.

In some implementations, the reactive fluid comprises hydrogen gas applied at a specified pressure above an ambient pressure. In some implementations, the pressure is achieved by electrochemical compression.

In some implementations, there is no measurable crossover liquid permeating through the separator from a positive electrode side to a negative electrode side.

BRIEF DESCRIPTION OF THE DRAWINGS

The foregoing aspects and others will be readily appreciated by the skilled artisan from the following description of illustrative embodiments when read in conjunction with the accompanying drawings.

FIG. 3A illustrates charge and discharge polarization, and FIG. 3B illustrates AC impedance at open-circuit.

FIG. 5A illustrates single woven Pt, expanded platinized Nb, or expanded platinized Ti mesh as (+) electrode, 0.6 M Ce and 4 M MSA at 65 mL min$^{-1}$, and boiled NR212 membrane. Figure SB illustrates enhancement of cell performance with addition of NSTF Pt layer on the (+) side of the membrane. Single Pt mesh (with or without NSTF) as (+) electrode, 0.6 M Ce and 5 M MSA at 70 mL min$^{-1}$, and boiled NR212 membrane.

FIG. 7A illustrates charge and discharge polarization. FIG. 7B illustrates peak discharge power density. Dashed line indicates flowrate was increased (300 mL min-t for 8 meshes, 450 mL min$^{-1}$ for 12 meshes) to achieve similar electrolyte velocity as for 4 meshes at 150 mL min$^{-1}$.

FIGS. 10A and 10B illustrate the impact of temperature on FIG. 10A polarization performance and FIG. 10B efficiency with a stack of 12 Pt meshes as (+) electrode, 0.6 M Ce and 5 M MSA at 150 mL min$^{-1}$, and boiled NR212 membrane. The room-temperature efficiency of the baseline cell is reproduced from FIGS. 4A-4C for comparison.

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

A Ce—$H_2$ system provides an unusually high open circuit voltage (1.5 to 1.7 V), which could enable high power and energy densities. A proof-of-concept for this system demonstrated 148 mW cm$^{-2}$ peak discharge power and 88% energy efficiency, and suggested that cerium kinetics limits cell performance. The Ce (+) electrode operates at potentials outside the stability window of water; however, extensive work on the aqueous Ce—Zn RFB indicates that appropriate solution chemistry and operating protocols can mitigate deleterious oxygen evolution. Due to its potential for high energy and high power densities, in various embodiments, this cell is explored to demonstrate a more optimized system is promising.

Figure 1:
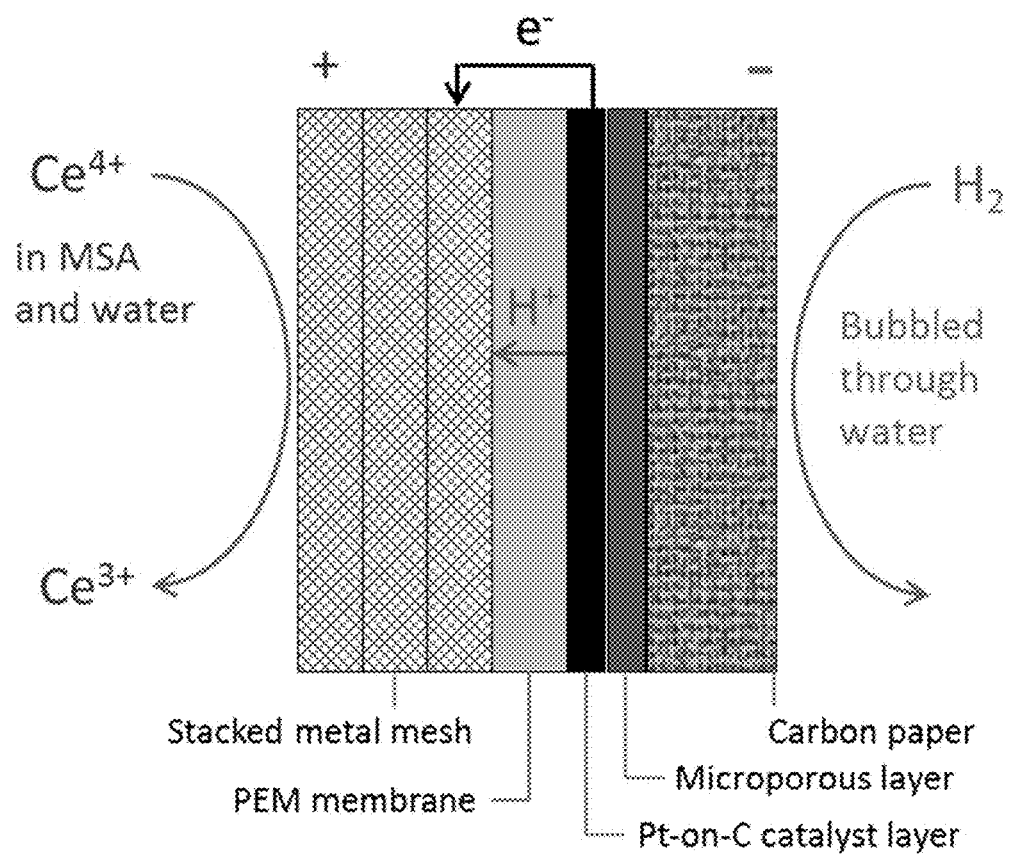
FIG. 1 illustrates a schematic of Ce—$H_2$ redox flow cell.

FIG. 1 illustrates a schematic of Ce—$H_2$ redox flow cell. The Ce—$H_2$ redox-flow system consists of an electrochemical cell that is fed reactants from storage tanks containing gaseous hydrogen (negative side) and an aqueous solution of $Ce^{4+}$ (positive side), as shown in FIG. 1. During discharge, hydrogen is oxidized to protons at the negative electrode. The protons pass through an ion-conducting membrane and react with Cerium(IV) methanesulfonate at the positive electrode to produce Cerium(III) methanesulfonate and methanesulfonic acid (MSA). The electrochemical reactions are shown below with the forward direction corresponding to discharge and the reverse to charge. Note that the potential for Reaction 2 depends on solvent type and concentration.

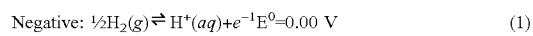

Negative: $\frac{1}{2}H_2(g) \rightleftharpoons H^+(aq) + e^{-1} \quad E^0 = 0.00$ V       (1)

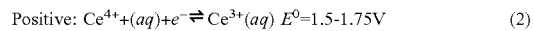

Positive: $Ce^{4+}(aq) + e^- \rightleftharpoons Ce^{3+}(aq) \quad E^0 = 1.5\text{-}1.75$V      (2)

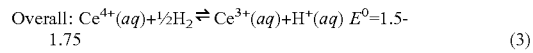

Overall: $Ce^{4+}(aq) + \frac{1}{2}H_2 \rightleftharpoons Ce^{3+}(aq) + H^+(aq) \quad E^0 = 1.5\text{-}1.75$      (3)

The promise of the high OCV offered by the Ce—$H_2$ couple is tempered by the relatively low current density reported for aqueous cerium electrochemistry on Pt catalyst in general, and moderate power density demonstrated for the Ce—$H_2$ cell specifically Hewa Dewage, et. al. Mater. Chem. A 3 (2015) 9446-9450. In various embodiments, we optimize the cell architecture and materials to achieve significantly improved power density and efficiency with commercially-available materials, and find that future improvements may require development of new cerium electrocatalysts and electrode architectures.

Experimental Methods

Cells were assembled and tested using 10 $cm^2$ Fuel Cell Technologies hardware and equipment discussed in detail elsewhere. A graphite serpentine flow field was used on the negative side (Fuel Cell Technologies). Serpentine or flow-through Niobium flowfields were used on the positive side to avoid carbon oxidation or metal corrosion (Treadstone Technologies, Inc.). The (+) electrode material was Pt woven mesh (Alfa Aesar, 0.17 mm thick, 52 mesh, 0.1 mm diameter wire), Ti woven mesh (Alfa Aesar, 0.22 mm thick, 50 mesh, 0.102 mm diameter wire), platinized titanium expanded mesh (Metakem type G, 4×2 mm diamond holes between 0.5×0.5 mm strands), platinized niobium expanded mesh (Gold Plating Services, 3×1.5 mm diamond holes between 0.3×0.15 mm strands), or nanostructured thin-film (NSTF) platinum catalyst layer (3M Company). The (−) electrode was 0.4 mg/$cm^2$ Pt/C printed on Sigracet GDL 24BC gas-diffusion layer (GDL), provided by Ion Power. Nafion 212 membranes were used, except where noted. Membranes were pretreated by boiling successively in 3% $H_2O_2$, DI water, 0.5 M sulfuric acid, and DI water for 1 h each, except where noted. The peroxide boiling step was skipped for NSTF-coated samples. Boiled membranes were assembled into the cell in the hydrated state to maximize conductivity, as crossover was found not to be a dominant concern for this system, as discussed below. Thickness of the incompressible gaskets around the active cell materials was chosen to achieve 20 to 25% compression of the (−) electrode upon assembly.

Cells were operated with hydrogen bubbled through water (200 sccm) and 0.6M cerium methanesulfonate with 3 to 6 M MSA solution (150 ml $min^{-1}$), except where noted. Hydrogen pressure was controlled with a backpressure regulator on the cell exhaust line. The (−) hydrogen exhaust was passed through a closed-bottom tube to collect any crossover liquid coming through the membrane from the (+) side; however, typically no liquid was observed, and the (−) electrode was found dry upon cell disassembly. Polarization curves (5 to 30 mA/$cm^2$ steps of 10 s each), AC impedance (at OCV), and cycling efficiency curves according to a protocol discussed elsewhere (typically with voltage limits of 0.2 to 1.9 V), were obtained with a Bio-Logic VMP3 potentiostat. Before testing, solutions were charged by holding the cell at 2 V until the theoretical charge required for 100% state of charge was achieved (the charging current also dropped significantly at the end of charge). Cerium utilization was determined from coulometry during cell operation. For each current density of interest, the cell was charged and then discharged, and the discharge capacity was used to determine the amount of cerium utilized, which was then compared to the total amount available (calculated from solution volume and concentration). Elevated-temperature experiments were conducted with cartridge heaters and a thermocouple in the cell hardware, and the solution tank submerged in a heated water bath.

Hydrogen gas pressure may also be increased by a mechanical pump or other mechanism or may be controlled, increased or decreased on the output side by increase/decrease of an output orifice.

Various cerium salts were screened for use in solution preparation. Solutions were prepared by adding the salt to water, and then slowly adding MSA. Cerium nitrate and cerium sulfate were ruled out based on observation of low solubility. Cerium carbonate was the most favorable, as it dissolved completely and produced a clear solution after off-gassing $CO_2$ via the conversion to cerium methanesulfonate. For 0.6 M Ce solutions, greater than 1 M MSA was required to achieve complete dissolution, and MSA concentrations in the range of 2 to 6 M were tested. For 4 M MSA, a range of cerium concentrations was tested; for 0.2 to 0.6 M Ce, compete solubility was achieved, but for 0.8 and 1 M Ce, precipitation was observed during cell operation. Furthermore, it was found that charging various solutions by holding the cell potential at 2 V until the current dropped to close to zero caused precipitation. Therefore, the typical cycling protocol charged the cell to lower voltage cutoff with no prolonged constant-voltage hold to avoid precipitation (see below).

Solution conductivity was assessed with a Symphony 4-probe conductivity cell (VWR Scientific) and Orion Star portable conductivity meter (Thermo Scientific).

Results and Discussion

Cell Operation

Figure 2:
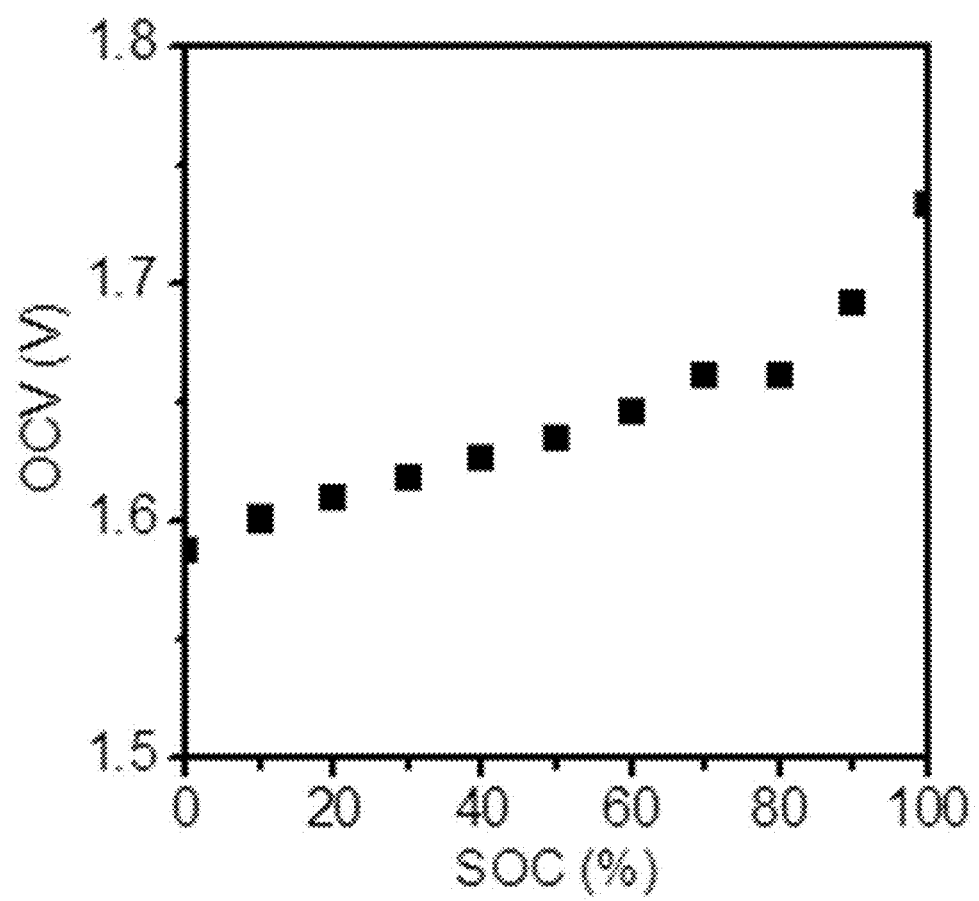
FIG. 2 illustrates open-circuit voltage variation with state of charge for 0.6 M Ce and 4 MMSA.

FIG. 2 illustrates open-circuit voltage variation with state of charge for 0.6 M Ce and 4 M MSA.

Aqueous cerium solutions were prepared from $Ce^{3+}$-carbonate, so the solution was first introduced into the cell in the fully discharged state (0% SOC). Before obtaining cell performance data, the solution was fully charged to roughly 100% SOC (all $Ce^{4+}$), during which the clear starting solution turned dark yellow. The OCV increases roughly linearly from 1.59 V at 0% SOC to 1.73 V at 100% SOC, as shown in FIG. 2. Clearly, a voltage cutoff limit above 1.73 V is required to achieve complete charging, and limits between 1.8 and 2.0 V were explored, as discussed below.

Figure 3A:
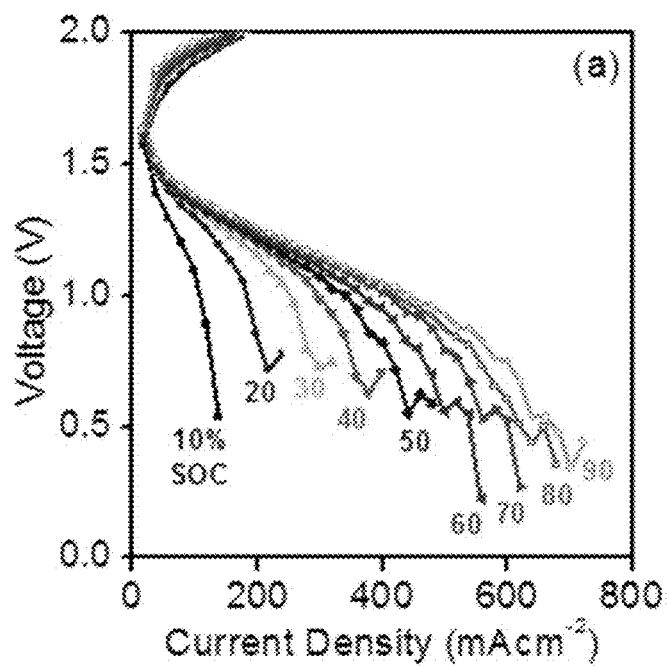
FIGS. 3A and 3B illustrate performance variation with state of charge for a stack of 4 Pt meshes as (+) electrode, 0.6 M Ce and 4 M MSA at 65 mL min$^{-1}$, and boiled NR212 membrane.
Figure 3B:
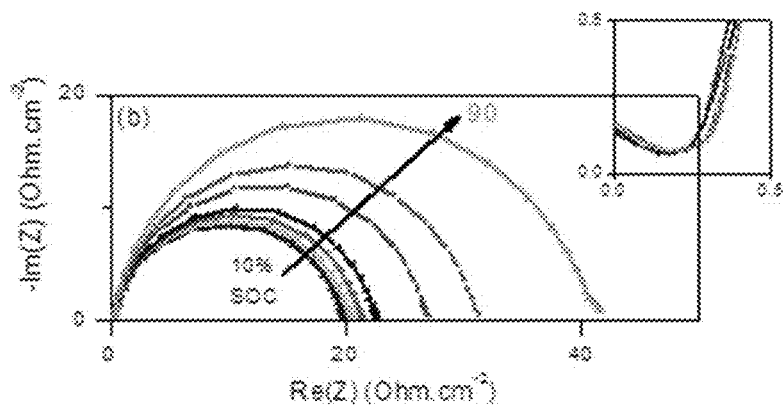

FIGS. 3A and 3B illustrate performance variation with state of charge for a stack of 4 Pt meshes as (+) electrode, 0.6 M Ce and 4 M MSA at 65 mL $min^{-1}$, and boiled NR212 membrane.

FIG. 3A illustrates charge and discharge polarization, and FIG. 3B illustrates AC impedance at open-circuit.

Cell performance varies significantly with SOC as shown in FIGS. 3A and 3B. Charge performance decreases and discharge performance increases with increasing SOC, following the variation in $Ce^{3+}$ and $Ce^{4+}$ concentrations (see FIG. 3A). The shape and trend of the discharge limiting current suggests significant $Ce^{4+}$ concentration polarization at high current density. Significant activation potential is evident in the low-current region, similar to the all-vanadium cell and in contrast to the $Br_2$—$H_2$ cell, which exhibits fast kinetics and linear, ohmic-dominated charge and discharge curves.

Note that the hydrogen concentration at the (−) electrode does not change with variations in SOC as excess hydrogen flows through the cell during operation, suggesting that the activation polarization arises at the (+) electrode. Impedance spectra (see FIG. 3B) show a small ohmic impedance and large polarization semicircle, consistent with the previous report that assigned the large low-frequency polarization to charge transfer at the cerium electrode. The ohmic impedance is only 20% of the value in the previous report, due to the thinner, pretreated membrane used here and discussed below.

Even so, the ohmic impedance is 2 to 3 times higher than the membrane resistances seen in the $Br_2$—$H_2$, Fe—$H_2$, and vanadium RFB systems, consistent with a significant deviation of membrane properties in the presence of cerium-MSA solution. It is interesting to note that the trend of total impedance (at open-circuit) with SOC is opposite to the trend of discharge performance, and the total impedance is much higher than the cell area-specific resistance (ASR) indicated by the slope of the discharge polarization curve. This is consistent with concentration polarization dominating when discharge current is applied. Further study of the impedance spectra as a function of current density is recommended.

Figure 4A:
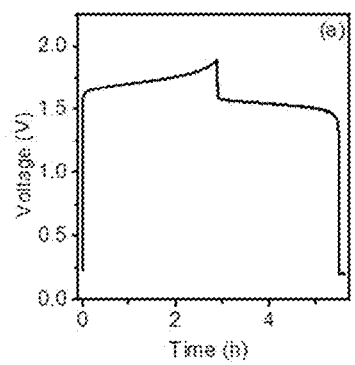
FIG. 4A illustrates full charge/discharge cycle at 10 mA cm$^{-2}$ with 1.9 V charge cut-off.
Figure 4B:
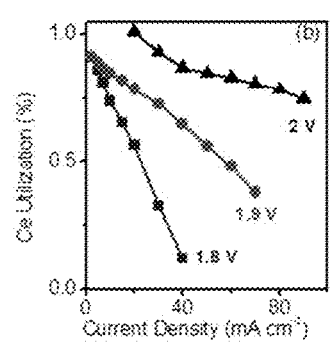
FIG. 4B illustrates impact of charge cut-off voltage on Ce utilization and FIG. 4C illustrates efficiency (thin lines—coulombic efficiency, dashed lines—voltage efficiency, thick lines—energy efficiency). Stack of 4 Pt meshes as (+) electrode, 0.6 M Ce and 4 M MSA at 65 mL min$^{-1}$, and boiled NR212 membrane.
Figure 4C:
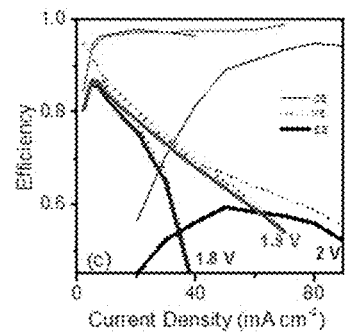

FIG. 4A illustrates full charge/discharge cycle at 10 mA cm$^2$ with 1.9 V charge cut-off. FIG. 4B illustrates impact of charge cut-off voltage on Ce utilization and FIG. 4C illustrates efficiency (thin lines—coulombic efficiency, dashed lines—voltage efficiency, thick lines—energy efficiency). Stack of 4 Pt meshes as (+) electrode, 0.6 M Ce and 4 M MSA at 65 mL min$^{-1}$, and boiled NR212 membrane.

Cell efficiency during constant-current cycling was assessed by adapting protocols discussed elsewhere. A typical charge-discharge cycle is shown in FIG. 4A. Both half-cycles show a featureless sloping plateau, consistent with the monotonic OCV and performance dependence on SOC (FIGS. 2 and 3A). There is a sharp decrease in voltage at the end of discharge, consistent with nearly complete conversion to $Ce^{3+}$ (0% SOC). In contrast, the end of charge increases in slope, but does not rise rapidly as would be expected in the case of complete conversion to $Ce^{4+}$.

This suggests that the charging process limits utilization (100% SOC is not achieved). Increasing the charge voltage limit was explored as a way to increase utilization, and FIG. 4B shows it to be quite sensitive. Increasing to 1.9 V limit significantly increases utilization, especially at higher current density where ohmic and kinetic overpotentials are significant contributors to cell potential and cause the limit to be reached at lower SOC.

Near complete utilization (100% SOC) is achieved only for a 2 V limit. For lower voltage limits, self-discharge (discussed below) limits the maximum utilization achieved at low current density. This sensitivity of utilization is important from a system-design perspective, as low utilization drives up the cost of storage capacity (for both cerium and storage-tank expenditures).

The voltage cutoff limit was also found to be important for energy efficiency, as shown in FIG. 4C. The general shape of the energy-efficiency curves is similar to those for $Br_2$—$H_2$ and Fe—$H_2$ redox-flow cells; low coulombic efficiency at low current (typically caused by crossover of active species) and low voltage efficiency at high current (caused by cell overpotentials) result in an optimum energy efficiency at an intermediate current density. With a 2 V limit, severely reduced ohmic efficiency causes less than 60% peak energy efficiency to be achieved.

We suspect this is due to the oxygen-evolution reaction (OER) at high voltage competing with cerium oxidation; evolved oxygen is released from the system and charge associated with the OER is not recovered during discharge. This is consistent with ex-situ 3-electrode cyclic voltammetry evaluation using a Pt mesh in the cerium-MSA solution, for which rapidly increasing current was observed above 1.8 V vs Ag/AgCl (2.03 V vs SHE) and higher, with bubble formation. In contrast, for 1.8 and 1.9 V limits in that cell, coulombic efficiency above 97% is achieved over a wide range of current density.

At very low current density (below 5 mA cm$^{-2}$), crossover through the membrane and concomitant self-discharge reduces coulombic efficiency, as discussed below. In all cases, voltage efficiency limits energy efficiency at high current density. A peak energy efficiency of 87% and cerium utilization of 86% are achieved simultaneously with the 1.9 V limit, albeit at a low current density of 7 mA cm$^{-2}$. Based on the impact on both utilization and efficiency, we selected 1.9 V as the optimum charge voltage limit, and this was used for all further experiments.

It is worth noting that the charge voltage limit restricts the maximum charge current density as clearly seen in FIG. 3a, so asymmetric charge/discharge current density may be required in a real system. For example, operation might include low-current charge during off-peak times and high-current peak discharge.

Cell Materials and Architecture
Cerium (+) Electrode

Platinum is a common choice for previous studies of cerium-based flow cells, based on good activity for cerium oxidation and reduction, and stability at high potential (where oxidation of carbon electrodes is a concern). Previous proof-of-concept work on the Ce—$H_2$ flow cell utilized platinized titanium expanded mesh as the (+) electrode.

Figure 5A:
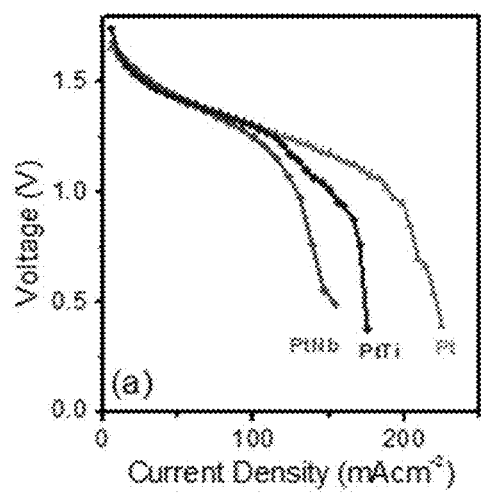
FIGS. 5A and 5B illustrate the impact of (+) type on performance.
Figure 5B:
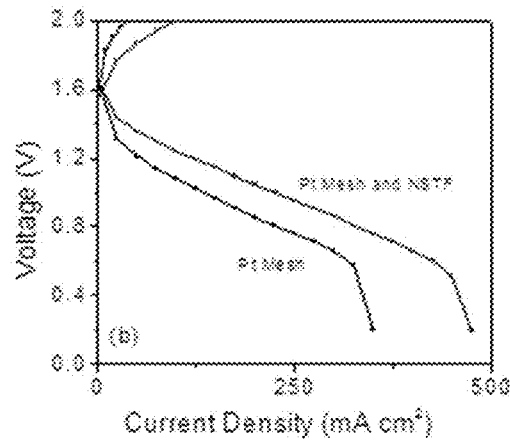

FIGS. 5A and 5B illustrate the impact of (+) type on performance. FIG. 5A illustrates single woven Pt, expanded platinized Nb, or expanded platinized Ti mesh as (+) electrode, 0.6 M Ce and 4 M MSA at 65 mL min$^{-1}$, and boiled NR212 membrane. FIG. 5B illustrates enhancement of cell performance with addition of NSTF Pt layer on the (+) side of the membrane. Single Pt mesh (with or without NSTF) as (+) electrode, 0.6 M Ce and 5 M MSA at 70 mL min$^{-1}$, and boiled NR212 membrane.

Here, we explore a variety of mesh types, as shown in FIGS. 5A, 5B. Platinized expanded Ti and Nb mesh provide similar, moderate performance. Considering that the surface area of the coarse expanded mesh exposed to the cerium electrolyte fluid is relatively low (estimated to be 0.8 cm$^2$ exposed surface per cm$^2$ of cell area), as most of the flat face is compressed into the membrane, we switched to woven Pt mesh composed of fine round wire (1.3 cm$^2$ per cm$^2$), which improved performance.

Although solid Pt mesh would be too expensive for implementation in a full-scale system, we expect that platinized Ti mesh with similar geometry would provide similar performance at greatly reduced cost. Cost-effective platinum electrodes require high surface area with relatively low loading. The NSTF electrode architecture developed by 3M for fuel cells and electrolyzers provides a thin (<1 μm), high surface-area electrode of Pt whiskers extending from and partially embedded in the membrane, with roughness factor an order of magnitude higher than for the mesh. Addition of an NSTF electrode layer to a single Pt mesh greatly increases performance, as seen in FIG. 5B, confirming that the cell performance is limited by Pt active area.

Figure 6:
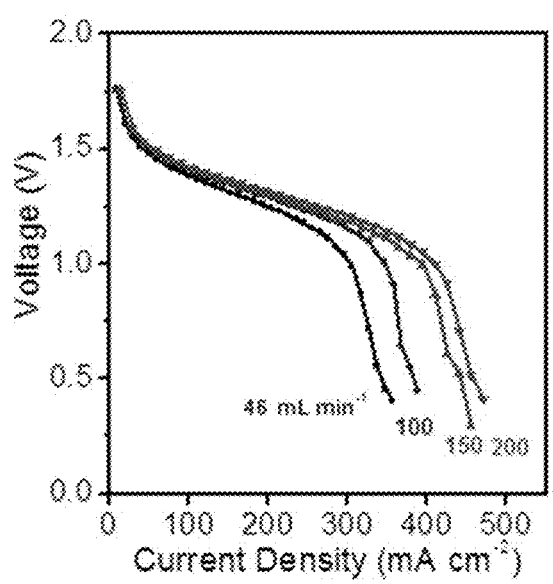
FIG. 6 illustrates the influence of flowrate on discharge performance. Stack of 4 Pt meshes as (+) flowthrough electrode, 0.6 M Ce and 4 M MSA, and boiled NR212 membrane.

FIG. 6 illustrates the influence of flowrate on discharge performance. Stack of 4 Pt meshes as (+) flowthrough electrode, 0.6 M Ce and 4 M MSA, and boiled NR212 membrane.

For all electrodes, there appears to be a mass-transport limit to the current density. As shown in FIG. 6, flowrate has a strong impact on the limiting current at low flowrate, and a flowrate above 100 mL min$^{-1}$ is required for the performance to be roughly independent of flowrate. Discharge current of 500 mA cm$^{-2}$ is equivalent to complete reduction of only 5 mL, min$^{-1}$ of cerium solution, so bulk depletion of reactant does not cause the limiting current (single-pass utilization varies from 8 to 2.5% at flowrates of 46 and 200 mL min$^{-1}$, respectively). Rather, sluggish diffusion of cerium-MSA complex to the active Pt surface is expected to give rise to concentration polarization (i.e., diffusion and not convection dominates at low flowrates). The cerium diffusion coefficient at relevant MSA concentrations is reported to be in the range 0.27 to 0.5 $10^{-6}$ cm$^2$ s$^{-1}$, about an order of magnitude lower than the diffusion coefficient of bromine and vanadium ions in redox flow-cell solutions, so significant mass-transport limitation is not surprising. Increasing the flowrate forces convection, alleviating mass-transport limitations.

The use of a flow-through electrode is also known to increase transport-limited performance in redox flow cells by forcing convection through the entire bulk of the electrode. A thick electrode is preferred in this geometry to reduce pressure drop.

Figures 7A, 7B:
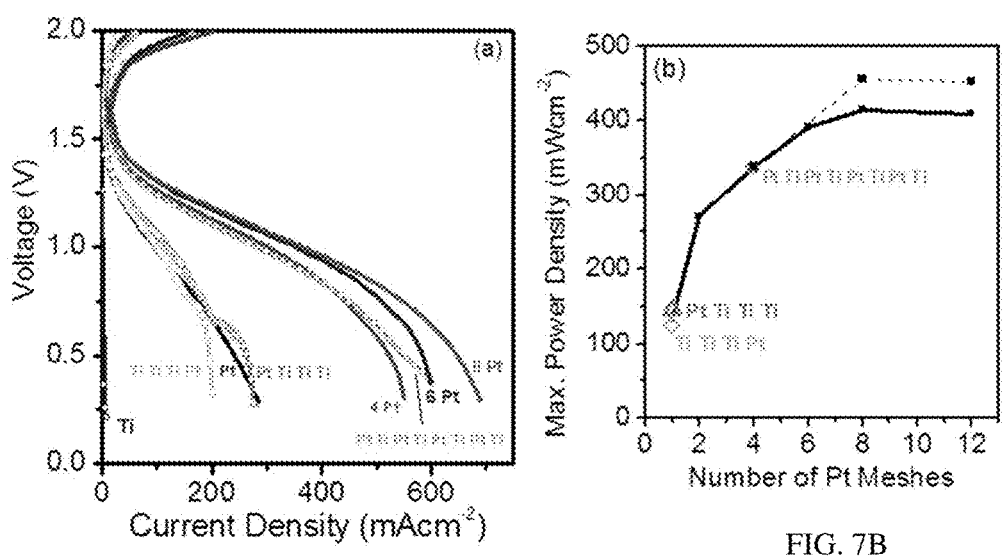
FIGS. 7A and 7B illustrate the impact of number of stacked meshes in the (+) electrode with 0.6 M Ce and 5 M MSA at 150 mL min$^{-1}$, and boiled NR212 membrane. Open symbols indicate cells in which Ti mesh was interspersed with the Pt mesh.

FIGS. 7A and 7B illustrate the impact of number of stacked meshes in the (+) electrode with 0.6 M Ce and 5 M MSA at 150 mL min$^{-1}$, and boiled NR212 membrane. Open symbols indicate cells in which Ti mesh was interspersed with the Pt mesh. FIG. 7A illustrates charge and discharge polarization. FIG. 7B illustrates peak discharge power density. Dashed line indicates flowrate was increased (300 mL min$^{-1}$ for 8 meshes, 450 mL min$^{-1}$ for 12 meshes) to achieve similar electrolyte velocity as for 4 meshes at 150 mL min$^{-1}$.

FIGS. 7A, 7B shows performance for a flow-through electrode with various stacks of multiple meshes. Increasing the number of stacked Pt meshes increases performance significantly. As the number of meshes increases, electronic bulk and contact resistances increase, ionic conduction path length in the electrolyte increases, reactive surface area increases, and superficial velocity (and therefore mass transport) in the electrode decreases. The total DC electronic resistance of dry cells with no membrane was found to be less than 0.03 Ωcm$^2$, and therefore insignificant. Electrolyte solution conductivity for 0.6 M cerium and 5 M MSA is 306 mS cm$^{-1}$, so ionic conduction in the sub-millimeter thick electrode accounts for at most ~10% of the ASR observed in the discharge polarization data. These drawbacks of a thicker mesh stack are overcome by the beneficial addition of Pt surface area, as clearly seen in FIG. 7B.

Interspersing inactive Ti mesh (with similar geometry to the Pt mesh) between the Pt meshes does not impact performance, confirming that the addition of Pt area overwhelms the disadvantages of a thicker electrode. The comparison of Pt—Ti—Ti—Ti (Pt at flowfield) vs. Ti—Ti—Ti—Pt (Pt at membrane) illustrates that ionic-conduction path length between the active Pt site and the membrane does not impact Pt-limited performance for low mesh number. Performance plateaus at high mesh number as the thickness of the electrode, as well as membrane and (−) electrode, become significant limitations relative to the high-area (+) electrode. Increasing the flow rate to maintain constant velocity in the electrode (relative to the 4-mesh case) increases performance slightly; mass transport is a small contribution to the limitation for the thick electrode in flow-through mode.

These results suggest cerium catalysis and mass transport both limit cell performance, consistent with the initial conclusions of previous work.

Hydrogen (−) Electrode

Excellent performance of the hydrogen electrode in other redox flow cells leads us to expect that it does not limit performance in the present system. To confirm this and optimize cell performance, various aspects of the hydrogen stream and (−) electrode were adjusted. The results are shown in FIGS. 11A-C, 12A-B. Varying hydrogen back-pressure between 0 and 1.7 bar, and moisture content between 0 and 100% relative humidity at room temperature, had no impact on cell performance, showing that the liquid at the positive electrolyte keeps the membrane hydrated.

The catalyst structure and platinum content of the (−) catalyst layer was varied between 4 mg cm$^{-1}$ Pt-black or 0.4 mg cm$^{-1}$ Pt-on-carbon catalyst layer, with little impact on performance. Pt-on-carbon may consist of Pt nanoparticles deposited on carbon particles. Pt nanoparticles/carbon particles in an ink may be deposited on the ion exchange membrane (IEM) or on the gas diffusion membrane. Deposition of the (−) catalyst layer on the membrane (catalyst-coated membrane, CCM) or on the microporous layer of the gas-diffusion layer (i.e., a gas-diffusion electrode, GDE) likewise did not affect performance. These results are in contrast to the $Br_2$—$H_2$ redox flow cell, for which cell performance is very sensitive to hydrogen and (−) electrode features, primarily due to adsorption of bromide ions on the Pt catalyst surface. These results suggest cerium adsorption on the (−) catalyst is not a concern in the present system, and are consistent with the (+) cerium electrode limiting cell performance to such an extent that subtle changes in (−) electrode performance are not apparent.

Membrane

Figure 8A:
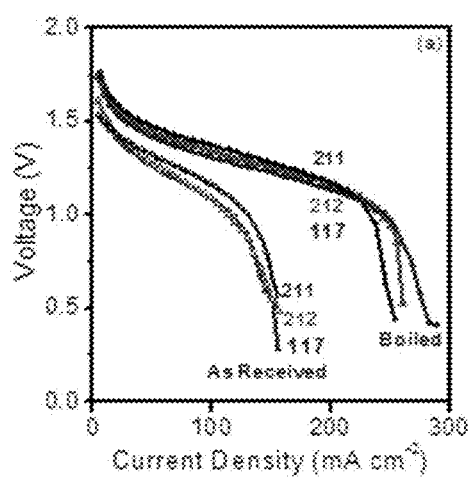
FIGS. 8A and 8B illustrate the effect of membrane thickness (N117, NR212, NR211) and pretreatment (as-received vs. boiled), FIG. 8A discharge polarization and FIG. 8B efficiency (thin lines—coulombic efficiency, dashed lines—voltage efficiency, thick lines—energy efficiency). Stack of 4 Pt meshes as (+) electrode, 0.6 M Ce and 4 M MSA at 65 mL min$^{-1}$.
Figure 8B:
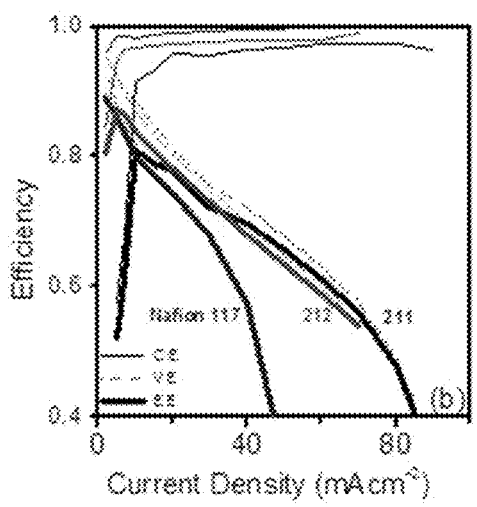

FIGS. 8A and 8B illustrate the effect of membrane thickness (N 117, NR212, NR211) and pretreatment (as-received vs. boiled), FIG. 8A discharge polarization and FIG. 8B efficiency (thin lines—coulombic efficiency, dashed lines—voltage efficiency, thick lines—energy efficiency). Stack of 4 Pt meshes as (+) electrode, 0.6M Ce and 4M MSA at 65 mL min$^{-1}$.

Pretreatment by boiling is known to increase significantly proton conductivity as well as transport of other species in redox flow cells. The impact of pretreatment and thickness is shown for various Nafion membranes in FIGS. 8A, 8B. The performance decreases slightly with membrane thickness, as expected from ionic resistance considerations. Discharge performance is highly sensitive to boiling pretreatment. These results suggest interfacial resistance (at the electrolyte-membrane interface) dominates over bulk membrane conductivity, and is highly dependent on pretreatment. Based on these results, pre-boiling was chosen as standard for all other cells assembled in this work.

The impact of membrane thickness on efficiency, for pre-boiled membranes, is shown in FIG. 8B. The maximum energy efficiency is limited by the coulombic efficiency, which is lower for thinner membranes and decreases rapidly at low current density. This behavior is similar to that observed in other redox-flow systems where crossover of the aqueous active species causes self-discharge. In those systems, transport of liquid through the membrane is observed. In both the Fe—$H_2$ and $Br_2$—$H_2$ systems, liquid crossover is high enough that the liquid must be collected from the hydrogen exhaust and returned to the (+) side for continuous functioning of the device. It is surprising, then, that no liquid was observed to cross through the membrane in the present Ce—$H_2$ system, even after continuous cycling operation for several days with the hydrogen exhausted into a liquid trap. It is possible that contact with the cerium-MSA electrolyte solution dehydrates the membrane to such an extent that bulk liquid flux is prevented (moderate dehydration of the membrane in contact with HBr is observed).

In the absence of bulk-liquid movement, we can envision $Ce^{4+}$ diffusion through the membrane from (+) to (−) side, reduction to $Ce^{3+}$ at the (−) side, and $Ce^3$ diffusion back to the (+) side as a mechanism for self-discharge, which is supported by the observed low coulombic efficiency when a microporous separator showing high liquid crossover was used. Cerium is known to be highly mobile in Nafion membranes during PEM fuel-cell operation, and similar mobility should be expected here. It is also possible that gas permeability of the membrane allows hydrogen to crossover to the (+) side where it could reduce $Ce^{4+}$ at the Pt electrode. The self-discharge current required to produce the observed coulombic efficiency for N117 is calculated to be in the range 0.04 to 0.1 mA $cm^{-2}$, according to the equations developed in Darling et. al., Electrochem. Soc., 163 (2016) A5014-A5022. This is similar to the 0.08 mA $cm^{-2}$ equivalent flux predicted from the hydrogen permeability data for boiled N117 available in the literature. Further detailed studies of the impact of cerium concentration and hydrogen pressure on the self-discharge rate are necessary to determine whether hydrogen or cerium crossover dominates. Regardless of the mechanism, it should be noted that the self-discharge current is extremely low, resulting in unusually high coulombic efficiency at low current density. For example, 99% coulombic efficiency is achieved for the present $Ce-H_2$ system with boiled NR212 membrane (FIG. 8B), whereas 65%, 86%, 90%, and 95-98% are achieved for the $Br_2-H_2$, $Fe-H_2$, $Ce-Zn$, and all-vanadium systems, respectively, at a similar current density.

A low-cost microporous separator was also tested (data shown in Supporting Information). Polarization performance was comparable to Nafion, however, a large amount of liquid crossover to the (−) electrode was observed. Bulk hydrogen gas transport to the (+) electrode was not observed. Very low coulombic efficiency occurred at low current density, consistent with reduction of crossover $Ce^{4+}$ at the (−) electrode. This supports the thought that $Ce^{4+}$ transport to the (−) electrode, if it occurs in Nafion membrane, results in self-discharge.

Electrolyte Composition

Aqueous solutions of cerium methanesulfonate and MSA are the standard for cerium electrochemical half-cells, although there is no clear optimum for cerium or MSA concentration. Cerium concentration affects reversibility, and solubility is known to depend on cerium oxidation state. MSA concentration influences reversibility of the cerium reaction, the extent of oxygen evolution side reaction, cerium solubility, and solution conductivity and viscosity.

Figure 9A:
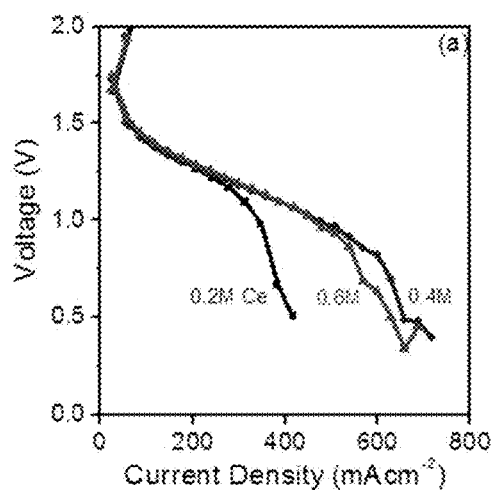
FIGS. 9A and 9B illustrate the variation of performance with FIG. 9A cerium concentration (for 4 M MSA, 65 mL min$^{-1}$), and FIG. 9B MSA concentration (for 0.6 M Ce, 180 mL min$^{-1}$). Solutions with 2 M and 6 M MSA showed poor charging performance, and were not tested further. Boiled NR212 membrane, and 4 Pt meshes as (+) electrode.
Figure 9B:
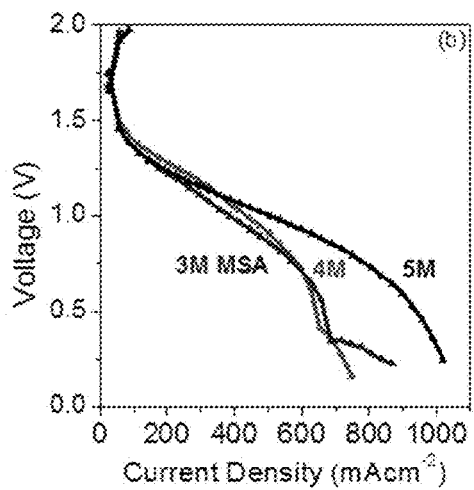

FIGS. 9A and 9B illustrate the variation of performance with FIG. 9A cerium concentration (for 4 M MSA, 65 mL $min^{-1}$), and FIG. 9B MSA concentration (for 0.6 M Ce, 180 mL $min^{-1}$). Solutions with 2 M and 6 M MSA showed poor charging performance, and were not tested further. Boiled NR212 membrane, and 4 Pt meshes as (+) electrode.

The impact of cerium concentration on performance is shown in FIG. 9A for solutions with 4 M MSA. Solutions with 0.4 and 0.6 M Ce provide similar performance. The limiting discharge current for 0.2 M Ce is lower, consistent with concentration polarization. Solutions with 0.8 M and 1 M Ce were also tested, however, precipitation was observed during charging and the performance results were therefore not reliable or reproducible. To select between 0.4 M and 0.6 M Ce, efficiency was determined, and found to be nearly identical (comparable to the data for 1.9 V cutoff in FIG. 4C). Therefore, 0.6 M Ce was chosen as the standard concentration, based on its higher volumetric energy density.

Following Nikiforidi et. al., Electrochimica Acta 141 (2014) 255-262, addition of 0.5 M HCl or $H_2SO_4$ to MSA was tested, but did not have a significant impact on cell performance. Complete replacement of MSA with $H_2SO_4$ was also evaluated, but cerium solubility and cell performance were both reduced. The impact of MSA concentration on performance is shown in FIG. 9B for solutions with 0.6 M Ce. Solutions with 2 M and 6 M MSA showed poor charging performance, and were not tested further. The discharge performance for 5 M MSA exceeded that of 3 M and 4 M MSA.

Temperature Dependence

Cell performance is expected to improve with operating temperature, as many properties are temperature-dependent, including transport properties, solution viscosity, and electrochemical kinetic parameters. Drawbacks to elevated temperature include the need for thermal insulation or preheating of the reactants, and reduced cerium solubility above 40 to 60° C. (depending on solvent).

FIGS. 10A and 10B illustrate the impact of temperature on FIG. 10A polarization performance and FIG. 10B efficiency with a stack of 12 Pt meshes as (+) electrode, 0.6 M Ce and 5 M MSA at 150 mL $min^{-1}$, and boiled NR212 membrane. The room-temperature efficiency of the baseline cell is reproduced from FIGS. 4A-4C for comparison.

FIGS. 10A, 10B shows that performance increases dramatically from room temperature to 60'C. Charge current of 373 mA $cm^{-2}$, discharge current of almost 1.5 A $cm^{-2}$, and peak discharge power density of 895 mW $cm^{-2}$ are achieved at 60° C. This greatly exceeds the performance of the present pre-optimized cell (see FIGS. 5A, 5B) and previously reported $Ce-H_2$ system, as well as the $Fe-H_2$, $V-H_2$, and other Ce-based redox flow cells including Ce—V, Ce—Pb, $Ce-BH_4$, and Ce—Zn. The efficiency improvement provided by the combination of cell optimization of the preceding Sections and elevated temperature is also substantial. The coulombic efficiency is reduced slightly at elevated temperature, consistent with increased transport of crossover species, but the substantial increase in cell performance more than offsets this with an overall dramatic increase in energy efficiency. Peak energy efficiency of 90% is achieved at 30 mA $cm^{-2}$, but more importantly, the maximum current density at which an energy efficiency of 85% or greater is possible increased from 15 to 60 mA $cm^2$, although this is still below some of the other systems in terms of maximum current density at high efficiency. Peak discharge energy density of 21.4 Wh $L^{-1}$ is achieved at 100 mA $cm^{-2}$ and 50° C. This is similar to the conventional all-Vanadium system, and about half the energy density of advanced all-Vanadium and $Br_2-H_2$ systems.

Figure 11A:
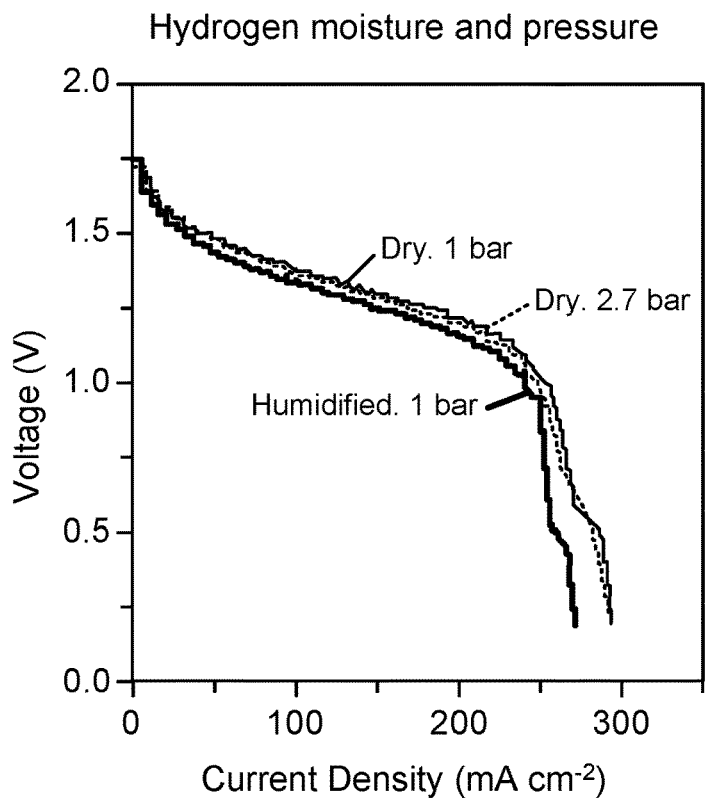
FIGS. 11A, 11B, and 11C illustrate various aspects of the hydrogen stream and (−) electrode were varied, with minimal impact on performance.
Figure 11B:
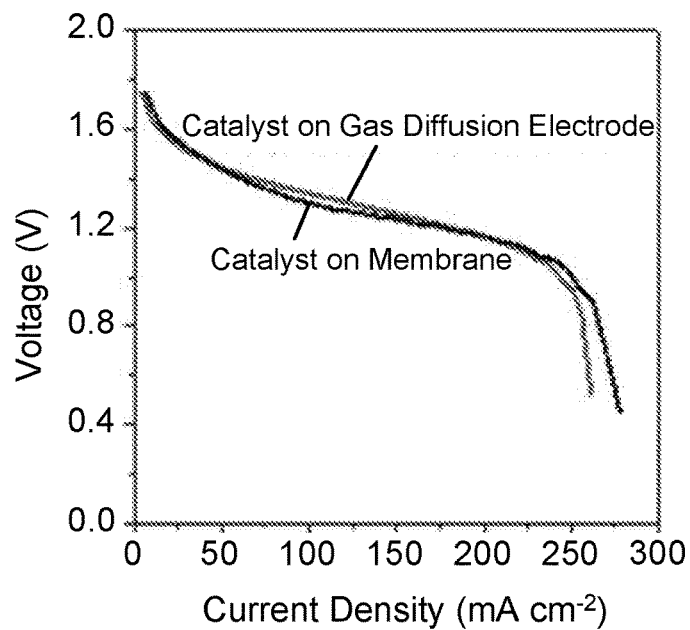
Figure 11C:
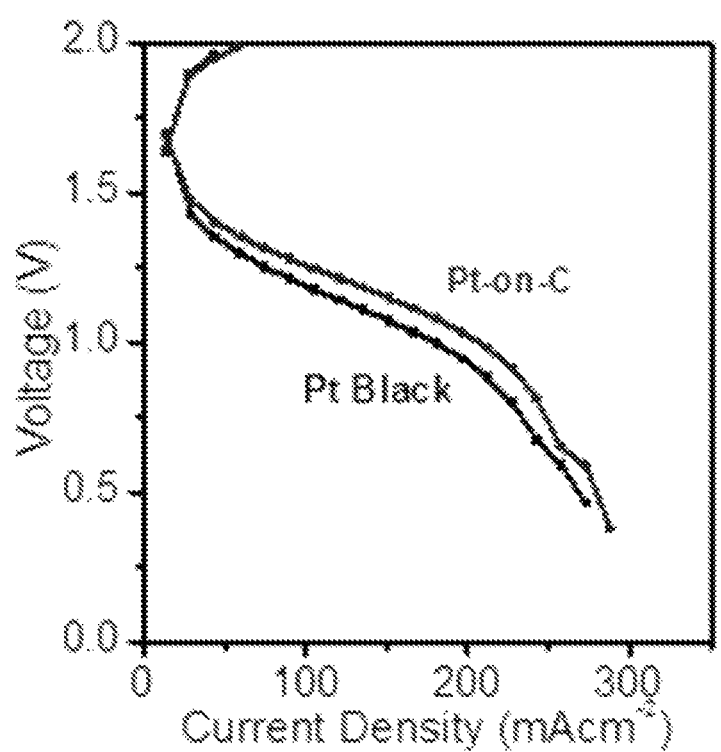

FIGS. 11A, 11B, and 11C illustrate various aspects of the hydrogen stream and (−) electrode were varied, with minimal impact on performance.

Figure 12A:
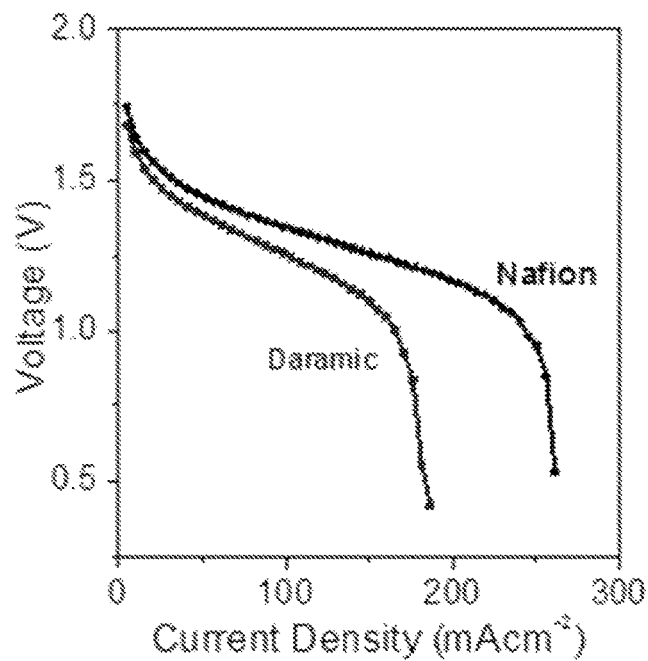
FIGS. 12A and 12B illustrate a comparison of Daramic microporous separator to boiled Nafion NR212 membrane, with 0.6 M Ce and 4 M MSA. During cycling with Daramic membrane, crossover liquid was recovered from the hydrogen exhaust and returned to the (+) tank, assuring that cerium was not removed from the system. A large amount of liquid crossover to the (−) electrode was observed. Bulk hydrogen gas transport to the (+) electrode was not observed. Very low coulombic efficiency occurred at low current density, consistent with reduction of crossover $Ce^{4+}$ at the (−) electrode. This supports the thought that $Ce^{4+}$ transport to the (−) electrode, if it occurs within Naftion membrane, would result in self-discharge.
Figure 12B:
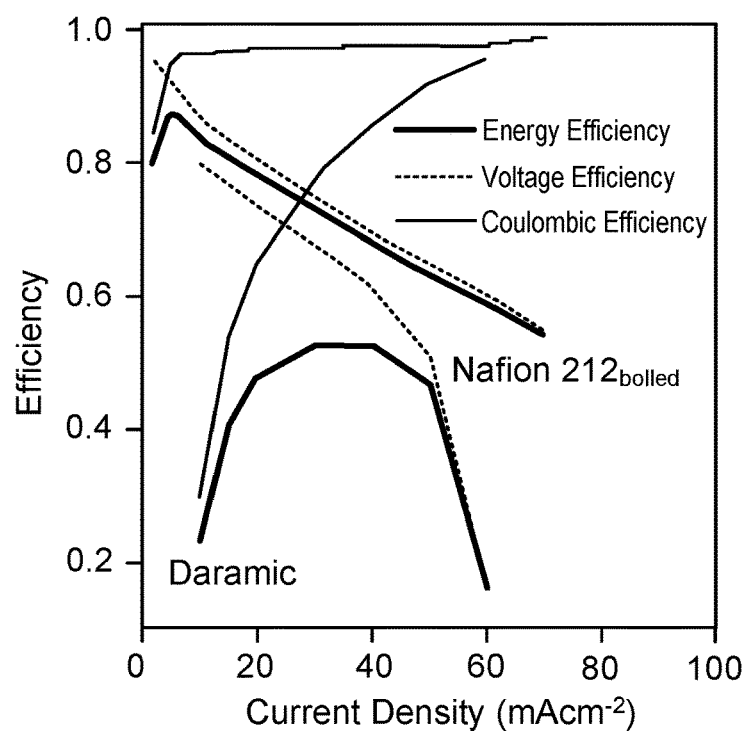

FIGS. 12A and 12B illustrate a comparison of Daramic microporous separator to boiled Nafion NR212 membrane, with 0.6 M Ce and 4 M MSA. During cycling with Daramic membrane, crossover liquid was recovered from the hydrogen exhaust and returned to the (+) tank, assuring that cerium was not removed from the system. A large amount of liquid crossover to the (−) electrode was observed. Bulk hydrogen gas transport to the (+) electrode was not observed. Very low coulombic efficiency occurred at low current density, consistent with reduction of crossover $Ce^{4+}$ at the (−) electrode. This supports the thought that $Ce^{4+}$ transport to the (−) electrode, if it occurs within Nafion membrane, would result in self-discharge.

SUMMARY

The $Ce-H_2$ redox flow cell was optimized using commercially-available cell materials and chemicals. Various aspects of the (+) and (−) electrodes including electrolyte solution, membrane, and cell operation were systematically varied, leading to a cell performance greatly exceeding previous reports. Cell performance was found to be sensitive to upper charge cutoff voltage, membrane boiling pretreatment, MSA concentration, (+) electrode surface area and flow pattern, and operating temperature. Performance was relatively insensitive to membrane thickness, Ce concentration, and all features of the (−) electrode and hydrogen flow. A maximum discharge power of 895 mW cm$^{-2}$ was observed at 60° C. An energy efficiency of 90% was achieved at 50° C. and 30 mA cm$^{-2}$.

A unique and surprising feature of this cell is the very low self-discharge (high coulombic efficiency), and absence of visible liquid transport through the membrane, accompanied by a relatively high membrane resistance. Further detailed study of the interaction between aqueous Ce-MSA and PEM membranes would be interesting. It would appear that identifying a membrane with higher conductivity, even at the expense of higher crossover, would be beneficial for energy-storage efficiency.

The high potential of the Ce reaction relative to the window of water stability means that high charging current (high overpotential) cannot be tolerated due to inefficiency associated with the oxygen evolution side reaction. In practice, therefore, asymmetric charge/discharge current density may be required. Substitution of a non-aqueous electrolyte may also alleviate this issue.

Thus, the cerium-hydrogen redox flow battery is optimized using commercially-available materials. A maximum discharge power of 0.9 mW cm$^{-2}$ was observed at 60° C. An energy efficiency of 90% was achieved at 50° C.

Key points of novelty include: a 3-dimensional porous positive electrode comprising Pt catalyst; an electrode functional layer comprising fine Pt such as 3M nanostructured thin-film (NSTF) platinum catalyst layer (3M Company); an electrolyte preferred composition: 0.6M cerium, 5M MSA; a thin (0.025-0.05 mm), pre-boiled membrane; and operated at elevated temperature to achieve high power and current densities, and energy efficiency >85% at 50 mA/cm2 or higher current density.

What is claimed is:

1. A redox flow cell comprising:
   a separator;
   a negative electrode in contact with hydrogen gas;
   a liquid comprising approximately 0.6 M cerium and 3 M to 6 M methanesulfonic acid (MSA); and
   a positive electrode comprising at least one metal mesh layer in contact with the liquid, the negative electrode being isolated from the positive electrode by the separator.

2. The redox flow cell of claim 1, wherein the separator comprises a nanoporous separator.

3. The redox flow cell of claim 1, wherein the positive electrode comprises a three dimensional porous flow-through structure.

4. The redox flow cell of claim 1, wherein the positive electrode comprises a stack of metal mesh layers.

5. The redox flow cell of claim 1, wherein the positive electrode comprises between 1 to 12 metal mesh layers comprising woven platinum meshes.

6. The redox flow cell of claim 1, wherein the positive electrode comprises a nanostructured thin-film (NSTF) platinum catalyst layer.

7. The redox flow cell of claim 1, wherein the negative electrode comprises a catalyst layer and a gas diffusion layer, and wherein the catalyst layer is in contact with the separator.

8. The redox flow cell of claim 7, wherein the negative electrode further comprises a microporous layer, and wherein the microporous layer is disposed between the catalyst layer and the gas diffusion layer.

9. The redox flow cell of claim 7, wherein the gas diffusion layer comprises carbon paper.

10. The redox flow cell of claim 1, wherein the separator comprises a proton exchange membrane (PEM).

11. The redox flow cell of claim 1, wherein the separator is 0.025 millimeters to 0.05 millimeters thick, and wherein the separator comprises a membrane treated by boiling in water.

12. The redox flow cell of claim 1, wherein the liquid comprises approximately 0.6 M cerium and 5 M methanesulfonic acid (MSA).

13. The redox flow cell of claim 7, wherein the catalyst layer comprises a 0.4 mg cm$^{-1}$ platinum-on-carbon catalyst layer.

14. A method comprising:
   providing redox flow cell comprising:
      a separator,
      a negative electrode, and
      a positive electrode comprising at least one metal mesh layer, the negative electrode being isolated from the positive electrode by the separator;
   contacting the negative electrode with hydrogen gas; and
   contacting the positive electrode with a liquid comprising approximately 0.6 M cerium and 3 M to 6 M methanesulfonic acid (MSA), with electricity being generating when the hydrogen gas is oxidized and the cerium is reduced.

15. The method of claim 14, wherein the liquid comprises approximately 0.6 M cerium and 5 M methanesulfonic acid (MSA).

16. The method of claim 14, wherein the approximately 0.6 M cerium is produced by dissolving cerium (IV) methanesulfonate in water.

17. The method of claim 14, wherein the redox flow operates at a temperature range between 21° C. to 60° C.

18. The method of claim 14, wherein the redox flow cell operates at a temperature range between 50° C. to 60° C.

19. The method of claim 14, wherein there is no measurable crossover liquid permeating through the separator from a positive electrode side to a negative electrode side when the redox flow cell is in operation.

20. The method of claim 14, wherein the hydrogen gas is at a specific pressure above ambient pressure.

21. The method of claim 14, wherein the specific pressure of the hydrogen gas is obtained by electrochemical compression.

22. The method of claim 14, wherein the hydrogen gas is bubbled through water before contacting the negative electrode with the hydrogen gas.

23. The method of claim 14, wherein the negative electrode comprises a catalyst layer and a gas diffusion layer, and wherein the catalyst layer is in contact with the separator.

* * * * *